US012734349B2

(12) United States Patent
Haecker et al.

(10) Patent No.: US 12,734,349 B2
(45) Date of Patent: Sep. 15, 2026

(54) MEDICAL TREATMENT APPARATUS WITH OVERPRESSURE IN THE PORT

(71) Applicant: Fresenius Medical Care Deutschland GmbH, Bad Homburg (DE)

(72) Inventors: Juergen Haecker, Bad Homburg (DE); Burkard Keller, Bad Homburg (DE); Peter Kloeffel, Bad Homburg (DE); Martin Thys, Bad Homburg (DE); Nico Roemmelt, Bad Homburg (DE); Alfred Gagel, Bad Homburg (DE); Soeren Gronau, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 719 days.

(21) Appl. No.: 18/030,666

(22) PCT Filed: Oct. 6, 2021

(86) PCT No.: PCT/EP2021/077517

§ 371 (c)(1),
(2) Date: Apr. 6, 2023

(87) PCT Pub. No.: WO2022/074039

PCT Pub. Date: Apr. 14, 2022

(65) Prior Publication Data

US 2023/0398273 A1 Dec. 14, 2023

(30) Foreign Application Priority Data

Oct. 7, 2020 (DE) ......................... 102020126225.6
Oct. 7, 2020 (DE) ......................... 102020126226.4
Feb. 15, 2021 (DE) ......................... 102021103496.5

(51) Int. Cl.
*A61M 39/18* (2006.01)
*A61M 1/14* (2006.01)
(Continued)

(52) U.S. Cl.
CPC ............ *A61M 39/18* (2013.01); *A61M 1/154* (2022.05); *A61M 1/1601* (2014.02);
(Continued)

(58) Field of Classification Search
CPC .... A61M 39/18; A61M 1/154; A61M 1/1601; A61M 1/1621; A61M 39/16;
(Continued)

(56) References Cited

U.S. PATENT DOCUMENTS 5,066,286 A 11/1991 Ryan
6,234,538 B1 5/2001 Lauer
(Continued)

FOREIGN PATENT DOCUMENTS

DE 102010032179 1/2012
DE 102015102990 9/2016
(Continued)

OTHER PUBLICATIONS

International Search Report and Written Opinion in International Appln. No. PCT/EP2021/077517, mailed Feb. 8, 2022, 17 pages (with English translation).

*Primary Examiner* — Leslie R Deak
*Assistant Examiner* — Alessandro R Del Priore
(74) *Attorney, Agent, or Firm* — Fish & Richardson P.C.

(57) ABSTRACT

The present disclosure relates to a medical treatment apparatus which includes at least one port, a device for closing, a compressed-air source and a control device and/or closed-loop control device. The port serves to establish fluid communication between at least one fluid line of the treatment apparatus associated with the interior of a treatment apparatus and a connector of a fluid line of a disposable associated with the exterior of the treatment apparatus. The sealing device is designed as a rinsing cap and serves to seal an interior of the port with respect to an exterior of the
(Continued)

treatment apparatus. The compressed-air source is used to introduce air into the port along at least one sterile-air line. The control device and/or closed-loop control device is programmed to cause the compressed-air source to build-up and/or maintain a predetermined minimum overpressure in the sterile-air line, the compressed-air source and/or inside the port.

23 Claims, 5 Drawing Sheets

(51) Int. Cl.
*A61M 1/16* (2006.01)
*A61M 1/36* (2006.01)
*A61M 39/16* (2006.01)

(52) U.S. Cl.
CPC .......... *A61M 1/1621* (2014.02); *A61M 39/16* (2013.01); *A61M 1/3622* (2022.05); *A61M 1/367* (2013.01); *A61M 2205/18* (2013.01); *A61M 2205/3337* (2013.01)

(58) Field of Classification Search
CPC ................ A61M 1/3622; A61M 1/367; A61M 2205/18; A61M 2205/3337; A61M 2205/15; A61M 1/168; A61M 1/342; A61M 1/3643; A61M 1/1619; A61M 39/26; A61M 39/10
See application file for complete search history.

(56) References Cited

U.S. PATENT DOCUMENTS

| | | | | |
|---|---|---|---|---|
| 7,985,196 | B2 | 7/2011 | Kopperschmidt et al. | |
| 9,352,139 | B2 | 5/2016 | Reiter et al. | |
| 9,884,176 | B2 | 2/2018 | Fangrow | |
| 2005/0283132 | A1 | 12/2005 | Stanus et al. | |
| 2009/0261581 | A1 | 10/2009 | Schmidt | |
| 2010/0101573 | A1* | 4/2010 | Foley | A61M 16/06 128/205.24 |
| 2010/0270792 | A1 | 10/2010 | Lauer | |
| 2013/0025697 | A1 | 1/2013 | Blasek et al. | |
| 2014/0031754 | A1 | 1/2014 | Williams et al. | |
| 2014/0163489 | A1 | 6/2014 | Walti et al. | |
| 2015/0025437 | A1 | 1/2015 | Tomko et al. | |
| 2017/0080205 | A1 | 3/2017 | Lauer | |
| 2018/0008812 | A1 | 1/2018 | Roxas et al. | |
| 2018/0021561 | A1 | 1/2018 | Nelson et al. | |
| 2018/0050186 | A1 | 2/2018 | Lauer | |
| 2020/0016316 | A1 | 1/2020 | Heide et al. | |
| 2020/0100798 | A1* | 4/2020 | Levit | A61M 5/145 |
| 2021/0296149 | A1* | 9/2021 | Green | H01L 21/67383 |

FOREIGN PATENT DOCUMENTS

| | | | |
|---|---|---|---|
| DE | 102017106403 | | 9/2018 |
| DE | 102021129109 | A1 | 5/2023 |
| EP | 0966984 | A2 | 12/1999 |
| EP | 2595691 | | 5/2013 |
| EP | 3127565 | | 2/2017 |
| EP | 3524291 | | 8/2019 |
| JP | 2009-529392 | A | 8/2009 |
| WO | WO 2010/121751 | A2 | 10/2010 |
| WO | WO 2010/146614 | | 12/2010 |
| WO | WO 2012/010322 | | 1/2012 |

* cited by examiner 100
2002
185
S
51
M
51
I
Ø25,6
31
3
Ø6,5
32
Ø15,3
205
60,2
30,8
22
2001
2001
2005
2005
2007a
202
200
A
2015
2003
2013
204
2007b
52

MEDICAL TREATMENT APPARATUS WITH OVERPRESSURE IN THE PORT

CROSS-REFERENCE TO RELATED APPLICATIONS

The present application is the national stage entry of International Application No. PCT/EP2021/077517, filed on Oct. 6, 2021, and claims priority to Application No. DE 102021103496.5, filed in the Federal Republic of Germany on Feb. 15, 2021, and claims priority to Application No. DE102020126225.6 and DE102020126226.4, each filed in the Federal Republic of Germany on Oct. 7, 2020, the disclosures of which are expressly incorporated herein in their entirety by reference thereto.

TECHNICAL FIELD

The present disclosure relates to a medical treatment apparatus as described herein, to a method as described herein, to a control and/or closed-loop control device as described herein, and to a medical blood treatment as described herein; it further relates to a computer program product as described herein.

BACKGROUND

Medical treatment apparatuses regularly include one or more ports. Fluid lines are connected to these ports in order to guide liquids out of or into the interior of the medical treatment apparatus. If the lines intended to be for single-use, they are referred to as disposables.

An aspect of the present disclosure may be to propose another medical treatment apparatus having at least one such port. It is also intended to propose a method for preparing for the operation of or for operating a medical treatment apparatus, a control and/or closed-loop control device, a medical blood treatment apparatus, and a computer program product.

SUMMARY

In some aspects, a medical treatment apparatus (hereinafter also referred to as: treatment apparatus for short) includes at least one port for establishing a fluid communication between at least one fluid line of the medical treatment apparatus, which is assigned to, facing, or attributed to the interior of the treatment apparatus, and a connector of a fluid line of a disposable which when in use carries fluid. The at least one port can, purely optionally, be at the end of the substitute fluid line or form this. The fluid line of the disposable is not part of the treatment apparatus, but rather is assigned, facing or attributed to the exterior of the treatment apparatus within the scope of the present disclosure. The fluid line of the disposable can be, for example, a tubing set or a part thereof, a substitute fluid line or the like.

The medical treatment apparatus further includes a sealing device, which can in particular be embodied as a rinsing or flushing cap. The sealing device serves to close an interior of the port vis-á-vis the exterior of the treatment apparatus.

The medical treatment apparatus further includes a compressed-air source for introducing air or sterile air into the port. The introduction takes place along at least one sterile-air line, which can be a component of the treatment apparatus.

In addition, the medical treatment apparatus includes a control and/or closed-loop control device. The control and/or closed-loop control device is programmed to cause the compressed-air source to build-up and/or maintain a predetermined minimum overpressure in the sterile-air line, the compressed-air source and/or inside the port. The minimum overpressure is above atmospheric pressure.

The method according to the present disclosure for preparing the operation or for operating a medical treatment apparatus according to the present disclosure optionally encompasses pumping off liquid from the interior of the port, preferably using the ultrafiltration pump and/or with the sterile-air line open to the atmosphere or environment. The pumping off is preferably volume-controlled and/or preferably by discarding the liquid via the waste line.

The method according to the present disclosure encompasses the creation of a closed volume or space which includes the interior of the port or a partial volume thereof. This is achieved by including lines which are in fluid communication with the interior of the port. This volume can be closed by actuating components of the blood treatment apparatus, for example its pumps, valves and/or other actuators. Alternatively, initiating this step can also be encompassed in the method according to the present disclosure.

The method also encompasses generating the overpressure, e.g., at least the predetermined minimum overpressure, in the closed volume via the compressed-air source, which can be a compressor, for example.

According to the present disclosure, a control and/or closed-loop control device is proposed which is programmed to initiate the execution of the method according to the present disclosure in interaction with a medical treatment apparatus, in particular with a medical treatment apparatus according to the present disclosure.

A medical blood treatment apparatus according to the present disclosure is embodied in particular as a medical treatment apparatus according to the present disclosure and includes a control and/or closed-loop control device according to the present disclosure.

A computer program product, according to the present disclosure, includes a volatile, transient program code or one stored on a machine readable carrier, in order to configure a control and/or closed-loop control device of a conventional medical treatment apparatus in such a way that the latter becomes a medical treatment apparatus, in particular according to the present disclosure, with a control and/or closed-loop control device as defined or disclosed herein.

The term "machine readable carrier" as it is used herein, refers in certain embodiments of the present disclosure to a carrier, which contains data or information interpretable by software and/or hardware. The carrier may be a data carrier, such as a diskette, a CD, DVD, a USB stick, a flashcard, an SD card, an EPROM or the like.

Embodiments according to the present disclosure may include one, several or all of the following features in any combination, unless this is recognized as being technically impossible by the person skilled in the art.

In all of the aforementioned and following statements, the use of the expression "may be" or "may have" etc. is synonymous with "is preferably" or "has preferably," etc. respectively, and is intended to illustrate embodiments according to the present disclosure.

Whenever numerical words are mentioned herein, the person skilled in the art shall recognize or understand them as indications of numerical lower limits. Unless it leads the person skilled in the art to an evident contradiction, the person skilled in the art shall comprehend for example the specification of "one" as encompassing "at least one". This understanding is also equally encompassed by the present disclosure as the interpretation that a numerical word, for example, "one" may alternatively mean "exactly one", wherever this is evidently technically possible for the person skilled in the art. Both understandings are encompassed by the present disclosure and apply to all numerical words used herein.

Whenever spatial references such as "above", "below", "upper" or "lower" are mentioned here, the person skilled in the art, when in doubt understands these as a spatial indication with reference to the orientation in the attached figures and/or the arrangement of the port according to the present disclosure in its intended use.

Whenever an embodiment is mentioned herein, it is always an exemplary embodiment according to the present disclosure and is not understood to be limiting.

When it is disclosed herein that the subject-matter according to the present disclosure includes one or several features in a certain embodiment, it is also respectively disclosed herein that the subject-matter according to the present disclosure does, in other embodiments, likewise according to the present disclosure, explicitly not include this or these features, for example, in the sense of a disclaimer. Therefore, for every embodiment mentioned herein it applies that the converse embodiment, e.g. formulated as negation, is also disclosed.

In several embodiments, the port optionally includes, preferably in an end section thereof, a first fluid conduit encompassing or including a first lumen with a first end opening or opening plane, for example, through which fluid can flow in its longitudinal direction. The fluid conduit is provided for receiving and/or guiding a medical fluid and for establishing the fluid communication with the connector or the fluid conduit.

In some embodiments, the port optionally additionally includes a second fluid conduit provided further outside (relative to the port, in particular to the radial extent thereof) relative to the first fluid conduit. The second fluid conduit includes at least a second lumen and a second end opening or opening plane.

Preferably, the first fluid conduit is located further inside the port than the second fluid conduit, e.g., in a radial and/or axial direction of the port.

Preferably, the first end-side opening is located further inside in the port than the second end-side opening, whereby the first end-side opening of the first fluid conduit is arranged, at least in sections, in the second lumen of the second fluid conduit.

In several embodiments, the compressed-air source introduces air or sterile air, particularly into the second lumen.

In some embodiments of the medical treatment apparatus according to the present disclosure, the control device and/or closed-loop control device is programmed to cause the compressed-air source to build-up and/or maintain the predetermined minimum overpressure in the sterile-air line, the compressed-air source and/or inside the port when or precisely when a predetermined program section of a program run by the control device and/or closed-loop control device for controlling or regulating the treatment apparatus is reached.

The predetermined program section may, for example, require the port to be opened by removing the sealing device, e.g., the rinsing cap, or disconnecting the connector from the port, and may also inform the user of this. In this way, for example, when progress has been made in preparing the treatment or in the treatment itself, in which opening of the port is pending, a request to the compressed-air source to build-up pressure can be issued autonomously, i.e., automatically, and processed accordingly within the machine. In some embodiments the medical treatment apparatus according to the present disclosure further includes a detection device. The detection device serves to recognise that or if an action to close the previously open and/or to open the previously closed second end opening of the port vis-A-vis the exterior of the treatment apparatus is about to happen, is taking place or has just taken place. It is further configured to emit a corresponding signal to the control device and/or closed-loop control device.

Such a signal can be an electrical signal, converted into one, or any other signal which is used for communication between components of a treatment apparatus, its actuators and its control or regulation. In these embodiments, the control and/or closed-loop control device is programmed to receive the signal emitted by the detection device, and in response to this or triggered by this, to establish or ensure a predetermined minimum overpressure in the sterile-air line, in the compressed-air source and/or in the port or in its second fluid, if present, in particular dependent on the signal emitted via the detection device or triggered by this.

In some embodiments, the compressed-air source is a compressor and/or a compliance vessel or includes a compressor and/or a compliance vessel.

In some embodiments, the compressed-air source includes both a compressor and a compliance vessel, e.g., with a non-return stop, in particular a check valve, provided between the two.

The non-return stop advantageously prevents compressed-air from flowing back from the compliance vessel in the direction of the compressor. The non-return stop can, for example, be a non-return valve.

The reaction time of the compressor can be bridged via the compliance vessel. When the port is opened, for example by disconnecting a fluid line connected to the port via a connector or by removing the sealing device, the overpressure prevailing inside the port is completely relieved within a very short time (usually <30 ms), even before the movement with which the connector or the sealing device was fully removed has ended. Due to and during the still continuing movement of the connector or the sealing device when they are separated from the outlet of the port, unwanted inflow of air from the outside of the port or the treatment apparatus into the inside of the port could occur. However, the air flow, initially generated due to the compliance vessel being under overpressure, the minimum overpressure or more, and continued after a few milliseconds due to the power of the compressor, flows from the inside of the port toward the outside, i.e., outward, due to the overpressure inside the port generated by the compliance vessel and/or compressor. Thereby, this desired air flow also takes residual liquids out of the port and/or from the connector or the sealing device to the outside. The formation of water bridges between hygienically sensitive connection areas and non-sterile surfaces, which could affect the interior of the port, is thus prevented or at least reduced.

In some embodiments, the control device and/or closed-loop control device is programmed to not further increase the pressure in the sterile-air line, the compressed-air source and/or the port once the predetermined minimum overpressure is reached or to prevent or inhibit further build-up of pressure. The latter can be checked and/or regulated via pressure measurement and is used for the safety of the treatment apparatus in that damage caused by excessive pressure can be prevented.

In several embodiments, the detection device includes or is respectively connected to a pressure sensor and/or a switch, e.g., in signal communication.

In these embodiments, the pressure sensor is preferably arranged to determine the pressure prevailing in the sterile-air line, the compressed-air source, and/or the port or its second fluid conduit, and in this way to collect a pressure value, such as a pressure reading.

In addition, the detection device in these embodiments preferably evaluates a pressure profile or a pressure change that results from pressure values collected at different points in time and that can be calculated, for example, by the detection device.

Alternatively or additionally, the detection device may register the actuation of the switch to output the signal as set forth herein based on the evaluation of the pressure profile or the pressure change and/or based on the actuation of the switch.

Actuation of the switch, such as by the user, due to a mechanical release, a constraint, or the like, by or upon removing the connector from the port, or prior to removing the sealing device, such as the flush cap, may indicate an opening or pending opening of the port.

In some embodiments, the medical treatment apparatus further includes a pressure reducer.

The pressure reducer is preferably located in the sterile-air line between the compressed-air source and the port.

In several embodiments, the pressure reducer is arranged to adjust or limit the pressure downstream thereof to at least 20 hPa and at most 500 hPa, which may again be for safety.

In some embodiments, the control and/or closed-loop control device of the medical treatment apparatus according to the present disclosure is programmed to preferably initially cause negative pressure in the first lumen, and preferably only when negative pressure exists there, to cause overpressure in the second lumen, if present. This may in particular be carried out on receipt of the signal if a signal is provided.

In several embodiments, the control and/or closed-loop control device is programmed to create a predetermined overpressure in the sterile-air line, the compressed-air source, and/or the port.

In these embodiments, it (the control and/or closed-loop control device) is further programmed, after or once the overpressure has been generated, to determine a pressure drop—with the port closed or with the second opening closed—or a pressure drop rate and based on this to determine when pressure or overpressure is to be built up again using the compressed-air source in order to achieve or maintain at least or precisely the minimum overpressure in the port or in the compliance vessel.

The step of building-up the minimum overpressure or a pressure above the minimum pressure is preferably carried out automatically.

In several embodiments, the medical treatment apparatus further includes a negative pressure source in fluid communication with the port, in particular with the second lumen of the second fluid conduit, if present.

In these embodiments, the control device and/or closed-loop control device may be programmed to generate negative pressure in the port, in particular, for example, in its second lumen, via the negative pressure source or to lower a pressure prevailing in the port, in particular down to the minimum overpressure, but preferably not lower than this, particularly if the pressure in the sterile-air line, the compressed-air source and/or in the port exceeds a predetermined threshold or maximum pressure, which is above the minimum overpressure.

Suitable negative pressure sources include pumps, such as the ultrafiltration pump for example, which are or can be brought into fluid communication with the port, e.g., by opening corresponding valves, and which in turn are or can preferably be brought into communication with the atmosphere, a drain, or the like.

In some embodiments, a sterile filter is arranged in the sterile-air line between the compressor and the port, and/or between the atmosphere and the port.

In several embodiments, the sterile filter produces, causes, or allows a pressure drop of maximally 10 PSI (1 PSI=68.94757293178 hPa), e.g., of maximally 5 PSI.

A pressure drop, or pressure loss, the amount of which for example can be calculated using the known formulas, is understood here as the pressure difference that is generated between the front and rear of the sterile filter, or upstream compared to downstream of the filter, due to the fact that the flowing fluid must flow through the sterile filter. It can arise through wall friction and dissipation.

In certain embodiments, the method according to the present disclosure includes closing the opening of the sterile-air line that is open to the atmosphere.

Several embodiments of the method according to the present disclosure encompass, when a pressure value of the generated overpressure is detected or measured above the upper threshold or the maximum pressure, preferably after waiting for a stabilisation period, actively lowering or reducing the pressure as necessary, for example via the ultrafiltration pump, until the pressure is again below the upper threshold or the maximum pressure.

In some embodiments, the method optionally encompasses removing air from the balancing circuit of the treatment apparatus and further optionally venting the balancing circuit towards the drain. These steps may also be referred to as preparation steps.

In several embodiments, the method optionally includes venting the port and/or the dialysate outlet line via the compressor until atmospheric pressure is present within the sterile-air line and/or the port.

In certain embodiments, the method optionally encompasses venting the port by opening a fluid connection associated therewith to the atmosphere.

In some embodiments, the method includes initiating a pressure rise within the port and/or the connected sterile-air line until an upper threshold is reached, such as the minimum overpressure or a maximum pressure above the minimum pressure, for example 200 hPa. Preferably, the compressor is then stopped to prevent a further pressure increase.

In several embodiments the method according to the present disclosure encompasses measuring the pressure prevailing in the port and/or in the sterile-air line, ideally after or once a pre-determined stabilisation time has been allowed to elapse.

In these embodiments, determining a pressure loss or a pressure loss rate based on generated overpressure and measured pressure is further encompassed within the method.

In some embodiments of the method, the method further encompasses reducing the pressure via the ultrafiltration pump until the pressure is again below the upper threshold or the maximum pressure, in particular if or when while measuring a pressure value above the minimum overpressure, an upper threshold or a maximum pressure, for example 300 hPa, is measured.

In several embodiments, the method optionally encompasses adhering to a waiting time, e.g., of five seconds. It includes (following the optional waiting time) determining a first pressure value, e.g., a first average pressure value averaged over a predetermined duration, e.g., one second.

Adhering to a (further) waiting time of predetermined duration, e.g., 24 seconds, and determining (following the waiting time) a second pressure value, e.g., a second average pressure value averaged over a predetermined duration, e.g., one second, are also encompassed by the method in some embodiments.

In several embodiments, the method further encompasses calculating a repetition time, for example, according to the following formula:

$$T = 25 * 50 \text{ hPa}/((P1 - P2)),$$

where P1 is the first average pressure value, P2 is the second average pressure value, and 50 hPa is the allowable pressure drop until the next increase in pressure in the port. The 25 s result from the waiting time before determining the second average pressure value and the duration over which this is determined.

In these embodiments, after the calculated repetition time has elapsed, the pressure in the port and/or in the sterile-air line is increased again to or at least to the minimum overpressure via the compressed-air source, for example using the compressor.

In some embodiments, the method further encompasses repeatedly building-up pressure using the compressor at intervals corresponding to or calculated from the previously calculated repetition time.

According to the present disclosure, it is provided that all, several or some of the steps of the method which can be performed by machine can be initiated by the control and/or closed-loop control device of the treatment apparatus.

A fastening section, which fastens the port to or in the housing of the treatment apparatus, in some embodiments, preferably includes a, e.g., raised, edge which may protrude over adjacent housing sections, may be recessed relative to them, or may be flush with them. Additionally or alternatively, the second opening is optionally recessed relative to the edge or relative to adjacent housing sections. The latter may prevent entry of liquids that could reach the port from the outside, usually inadvertently, such as during cleaning of the housing or spillage of liquids by staff or the patient by allowing such liquids to be drained downwardly past the opening of the port.

The port entrance, or second opening, in some embodiments is recessed relative to the fastening section or to the edge thereof. The latter may also impede or prevent the entry of liquid from the outside.

In some embodiments of the port according to the present disclosure, the second end opening of the second fluid conduit includes a smaller external cross-sectional area or opening area than a cross-sectional area or opening area of the second lumen arranged further inside the treatment apparatus than the second end opening. Hereby, the outer diameter of the first fluid conduit is preferably constant, in particular in a region in which the cross-sectional area or opening area of the second lumen increases axially, in particular towards the interior of the port or treatment apparatus. In this way, on the one hand, a sufficiently large distance is created between the first opening of the first fluid conduit and the inner wall of the second lumen, which counteracts the formation of liquid bridges between the opening and the inner wall due to the sufficiently large distance created between these two. Droplets hanging between the opening and the inner wall advantageously break off due to the distances between the opening and the inner wall selected inside the port. On the other hand, the cross-sectional area of the second lumen does not correspond to the cross-sectional area of the second opening, i.e., the opening of the second lumen to the outside. When opening the sealing device, e.g., the rinsing cap, less force must therefore be applied by the user (due to the comparatively small circumferential area, which also forms the sealing surface) than if the second opening and thus also the sealing device had diameters such as those of the second lumen further inside the port.

In several embodiments, no section of an edge of the first fluid conduit which limits the first opening includes a distance from an inner wall which limits the second lumen, that is not at least 7 mm.

In some embodiments, this distance additionally or alternatively corresponds to at least 1.1 times, 1.5 times, or 2 times the difference between the radius of the outer peripheral surface of the first fluid conduit and the radius of the inner peripheral surface of the second opening, e.g., where side surfaces limiting it (e.g. in a longitudinal section as shown in FIG. 1 or FIG. 2) are parallel and/or at a constant angle to each other.

In some embodiments, the second opening is that region of the second lumen or the second fluid conduit where they limit side surfaces (e.g., in a longitudinal section as shown in FIG. 1 or FIG. 2) stand or are parallel to each other.

In some embodiments, the second lumen of the second fluid conduit includes at least one longitudinal section that is not limited (i.e., upwardly and downwardly, for example) by side walls that are parallel to each other and/or at a constant angle to each other. This longitudinal section is in some embodiments at least 3 mm long, e.g., at least 5 mm long, or at least 1 cm long. It lies optionally further outwards (with respect to the housing of the treatment apparatus or to the port) than the first opening. In this way, a distance is created between the inner wall of the second lumen and the first opening of the first fluid conduit, which counteracts fluid transfer between the two during treatment.

In several embodiments, the second lumen of the second fluid conduit of the port does not include a longitudinal section in the longitudinal direction thereof and/or does not have a longitudinal section over at least 90% of its length and/or does not have a longitudinal section with the exception of the section with the second opening, each of which is at least 3 mm long, e.g., at least 5 mm long, or at least 1 cm long, and lies optionally further outward than the first opening, which is or would be limited in a longitudinal section by parallel side walls and/or side walls at a constant angle to each other.

In some embodiments of the port, the second lumen includes a first cross-sectional area limited by side walls of that lumen. This is preferably smaller than any other cross-sectional area limited by the side walls of the second lumen, which lies further towards the interior of the second lumen than the first cross-sectional area, i.e., further inside the port or treatment apparatus than the first cross-sectional area.

In several embodiments of the port, the second lumen widens, at least in sections, toward the interior of the port or treatment apparatus.

In some embodiments, the second lumen includes at least three cross-sections, each of which has a larger cross-sectional area toward the interior of the port or treatment apparatus than the preceding one of those cross-sections.

In several embodiments, the second lumen does not include a circular cross-sectional area in at least one cross-section.

In some embodiments of the port according to the present disclosure, the first lumen terminates or opens into the first end opening in a funnel-shape or diverging shape.

In some embodiments, in at least one cross-section of the port, the cross-sectional area of the first lumen is not concentric with the cross-sectional area of the second lumen. Alternatively or additionally, the side walls of the cross-section limiting the second lumen are not uniformly spaced from a centre line of the first lumen extending longitudinally along the first lumen and/or the portions on the periphery of this cross-section are not all uniformly spaced from this centre line.

In some embodiments of the port, the second lumen includes at least one cross-sectional area that has a smaller extension in its transverse direction than in its height.

In several embodiments, the second lumen includes at least one opening, such as a groove, which is arranged on or in a sidewall limiting the second lumen and preferably extending in a circumferential direction of the second lumen or a portion thereof. The opening thereby preferably leads to an opening of the second lumen, which serves or can serve to connect the second lumen with a drain or waste line by a connector.

In some embodiments, the first end opening of the first fluid conduit is further towards the interior of the port than the second end opening of the second fluid conduit, i.e., it lies further inward. The first end opening of the first fluid conduit is at least 5 mm, e.g., at least 10 mm, or at least 15 mm further inside than the second end opening of the second fluid conduit.

In several embodiments, the cross-sectional area of the second lumen always and/or steadily increases in the axial direction from a cross-section in which the opening plane of the first end opening of the first lumen also lies to the entrance of the opening, e.g., to the front of the groove.

In some embodiments, the inner wall of the first lumen is shaped to converge or widen towards the first opening, at least in sections. The angle may be, for example, 2°.

In several embodiments, the wall or outer wall surrounding the connector lumen is shaped to diverge or taper toward the opening of the connector lumen, at least in sections. The angle may be 2°, for example.

In some embodiments, the inner wall of the first lumen and the wall or outer wall surrounding the connector lumen are inclined at identical angles with respect to the centre lines of their lumens.

In some embodiments, the first lumen tapers only in the first third of the first fluid conduit or only on the first 1.5 mm to 3 mm. For example, an opening angle of the first fluid conduit may be between 10° and 20°, e.g., 15°. The resulting insertion angle/chamfer/bevel can help to prevent unwanted contact of the front facing surfaces.

The sealing device, or the rinsing cap, which serves to temporarily close the second opening of the port, in some embodiments includes a front side facing the interior of the medical treatment apparatus when the sealing device is in use, which includes an axially and/or radially raised edge on its periphery.

In some embodiments, the sealing device further includes a first recess or first groove extending in or on its circumferential side.

In some embodiments, the sealing device, e.g., the rinsing cap, further includes a second recess or second groove extending in or on its circumferential side, preferably axially adjacent to the raised edge.

In some embodiments, the raised edge of the sealing device, here and hereinafter for example the exemplarily referred to rinsing cap, includes a section that is wedge-shaped or triangular in a longitudinal section of the rinsing cap. This section may describe an isosceles triangle and/or converge on either side of the tip at an equal angle. Therefore, in certain embodiments, it can be ensured that less residual liquid remains in the port after disconnecting the rinsing cap.

In several embodiments of the medical treatment apparatus according to the present disclosure, the pivot lever is arranged in order for it to pivot around the pivot axis into a third pivot position. In this third pivot position of the pivot lever, neither the receiving section for releasably receiving a rinsing cap nor the stop for temporarily preventing an axial separating movement for separating the connector of the disposable is arranged in axial direction in front of the second lumen of the port.

In some embodiments of the system, the rinsing cap includes an outer edge that is preferably round or includes a round edge section with an outer radius corresponding to a value between 90% and 99.9% of the inner radius of the first section of the edge of the treatment apparatus.

In several embodiments of the treatment apparatus, the pivot lever includes a recess or groove. It is designed for inserting a section of the edge of an end-plate or end-washer of the connector. The recess is provided so that by pulling on the pivot lever, e.g., on a handle piece thereof, the pivot lever not only releases the port, but also the connector is simultaneously removed from the port via the recess in which the edge of the end-plate or end-washer is inserted.

In some embodiments of the treatment apparatus, the port is received in the fastening section thereof such that a centre line of the first fluid conduit or the first lumen is inclined 4° or more degrees to a mounting surface of the medical treatment apparatus.

In some embodiments, the medical treatment apparatus includes a displacement device via which the pivot lever is translationally displaceable or guidable along the pivot axis. The displacement device may be part of the pivot lever. Preferably, the pivot lever can only be displaced or guided by the displacement device to a limited extent or only by a predetermined distance. For this purpose a limiting device can be provided. Preferably, the shifting or guiding takes place in use and/or without the use of tools.

In some embodiments, the port or the treatment apparatus have a return element, for example a spring. The return element serves to move the receiving section in a translatory manner and/or to preload the receiving section in an axial direction. Alternatively or additionally, the port or the treatment apparatus include a damper device for damping a translational movement brought about by the return element.

In several embodiments of the treatment apparatus, the dimensions of the rinsing cap are such that the first recess or groove and the second recess or groove of the rinsing cap are in fluid communication with each other when the rinsing cap is inserted into the port. Fluids can thereby preferably flow in an axial direction along the outside of the flush cap from the first groove or recess into the second groove or recess, or vice versa. The second groove or recess results from the particular design of the edge of the front facing surfaces of the rinsing cap as described in detail below.

The term “fluid conduit” as used herein, in certain embodiments of the present disclosure, generally refers to a physical or bodily arrangement of elements which are provided for receiving and/or conducting, guiding and the like fluids. Examples include pipes, tubes, ducts, conduits, chambers, fluid guiding devices, etc.

In certain embodiments of the present disclosure, the first fluid conduit is provided for guiding outwards or discharging a medical fluid out of an exit opening of the first fluid conduit (i.e., out of the port), for example, into the environment, into an exterior, into the connected disposable, etc.

In certain embodiments of the present disclosure, the term “medical fluid”, as used herein, generally refers to liquids such as dialysate, substitute fluid, drug solutions, priming and/or rinsing and/or sterilization fluids and the like, as well as gases, e.g., sterile air, and any combinations or mixtures thereof and therewith. In certain embodiments of the present disclosure, the medical fluid is suitable and/or intended or meant for extracorporeal blood treatment.

In certain embodiments of the present disclosure, the medical fluid is substitute fluid, and in some embodiments according to the present disclosure, substitute fluid produced on-line by a treatment apparatus.

A sealing device, as used in certain embodiments of the present disclosure, refers to a sealing device configured and/or provided to close or seal the port with respect to an exterior of the port, for example by closing or sealing its second opening of the second lumen, if present. For example, the sealing device may be a closure cap or a rinsing cap.

The sealing device may seal the port according to the present disclosure against an exterior in a fluid-tight manner. The lumens of the port may be in fluid contact with an interior of the sealing device.

In certain embodiments of the present disclosure, the sealing device is provided in order to enable or facilitate cleaning of the port.

The sealing device may be configured to pivot and/or slide automatically or automated.

In certain embodiments of the present disclosure, the port according to the present disclosure includes a hydrophilic coating at least in some sections or is made—in these sections—of a hydrophilic material.

In order to minimize droplets, for example during displacement or pivoting of the flush cap, in certain embodiments of the present disclosure a hydrophilic coating of the port and/or the sealing device may be preferred.

In some embodiments, the port according to the present disclosure is part of a machine-side substitute fluid system of the medical treatment apparatus.

In certain embodiments, the port is provided on the medical treatment apparatus inclined to the horizontal.

In certain embodiments, the port may be provided inclined to the horizontal within an angular range of 8°±3°.

In several embodiments according to the present disclosure, the port is arranged such that in at least one position (rinsing position, connection position, etc.) its first lumen includes an inclination to the horizontal as described above, at which inclination the free end of the first lumen is lower than other sections thereof. Such an inclination, especially also in combination with the optionally hydrophilic coating or optionally hydrophilic material of the inner wall of the second lumen, may promote a non-tearing formation of a film of residual liquid moving towards a connection for the drain or waste line. This can be discharged from the port via the drain or waste line with almost no residue.

In certain embodiments, the treatment apparatus according to the present disclosure is designed as an extracorporeal treatment apparatus, in particular as an extracorporeal blood treatment apparatus, such as a dialysis apparatus, in particular as a hemodialysis apparatus, hemofiltration apparatus, hemodiafiltration apparatus, or as an apparatus for adsorption, liver replacement therapy, apheresis, transfusion, and so on.

The device for introducing the sterile air may be provided at any location, in particular at any location of the second fluid conduit, but at a location different from the second opening or the free end of the second lumen.

In some embodiments, the port does not include a spring element, for example, to allow the first fluid conduit to be displaced in an axial direction within the port against the force of the spring.

In some embodiments, the port does not include a screw section and/or a thread provided to connect the disposable to the port.

In some embodiments, the outer diameter of the first fluid conduit is constant, at least in a free region of the first fluid conduit.

In some embodiments, the first end opening of the first fluid conduit of the port faces further toward the interior of the port than the second end opening of the second fluid conduit.

In several embodiments, the medical treatment apparatus includes a pivot lever arranged to pivot about a pivot axis thereof, the pivot lever which includes a stop for temporarily preventing an axial separation movement separating the connector of the disposable from the attachment section by or after pivoting the pivot lever to a second pivot position of the pivot lever. The stop is configured to limit rotation of the inserted connector around the longitudinal axis of its connector lumen, particularly in interaction with the end-plate or end-washer of the disposable.

Several or all embodiments according to the present disclosure may have one, more or all of the advantages mentioned above and/or below.

The present disclosure provides a treatment apparatus including fluidic interfaces in the form of one or more ports, which can advantageously satisfy the highest hygienic demands placed on medical treatment procedures.

Through the use of the present systems, methods, and devices, an environment which is as germ-free as possible at the connections between the disposable and the treatment apparatus can advantageously be ensured. This can help to prevent the introduction of germs into the patient’s blood and thus increase patient safety. This is a consequence of the further reduction of residual fluids in the area of the second fluid conduit of the port, which may be preceded by an initial emptying of the port by introducing air, which is why, for example, only a small amount of residual fluid (usually about 5 μl-10 μl) remains in the port.

A further advantage of the present devices, systems, and methods may be that germ transfer by aerosols onto the opening of the first fluid conduit, which may occur via dynamic negative and overpressure conditions with rapidly executed movements during the connection and disconnection of the disposable and sealing device, e.g., rinsing cap, even with very small amounts of residual fluid, is also reduced or prevented via the present disclosure.

During the opening of the port as the fluidic interface of the treatment apparatus, a preferably uninterrupted air flow is ensured from the interior of the port towards the exterior. The air flow advantageously prevents particle entry which could occur for example via liquids and/or air turbulences and may also include germs, into the sterile interior of the line system, in particular in the direction of the first end-side opening.

The present disclosure advantageously helps to easily eliminate or at least to reduce cross-contamination by pathogenic organisms possibly present at the interface, both in terms of design and method technology.

Areas of the sealing zones of the interfaces, especially those that are not reached during surface disinfection or by internal hydraulic disinfection, are advantageously protected from contamination by the present devices, systems, and methods.

BRIEF DESCRIPTION OF THE DRAWINGS

The present disclosure will be explained in the following with reference to the accompanying drawing. In the figures identical reference numerals designate the same or similar components.

FIG. 1 shows a port 100 of a medical treatment apparatus 2000 in a first embodiment.

Figure 1:
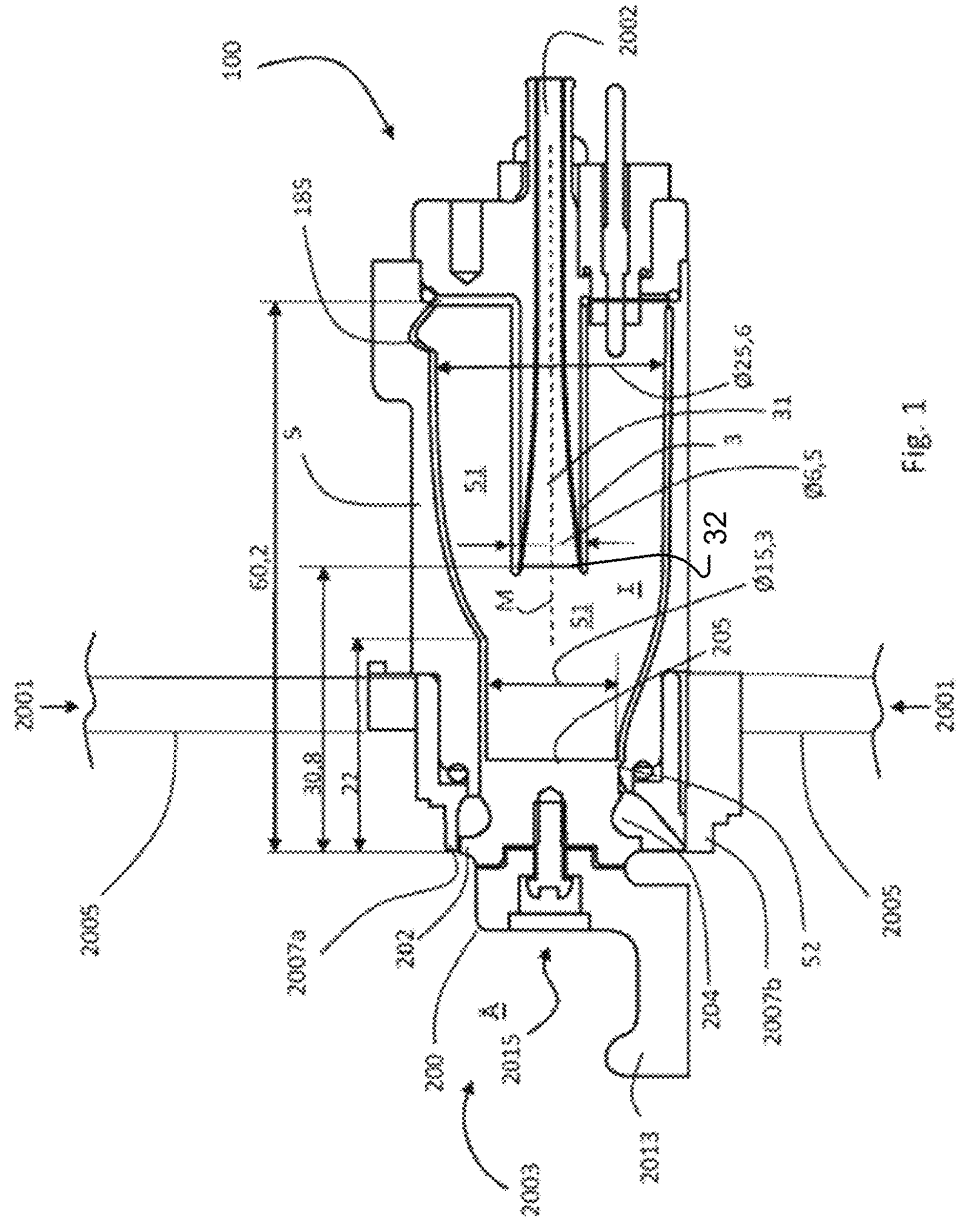
FIG. 1 shows a port of a medical treatment apparatus according to the present disclosure in a first embodiment.

The port 100 includes a first fluid conduit 3 with at least one first lumen 31 and a first end opening 32. The first lumen 31 can be flowed through in its longitudinal direction, indicated by its center line M. Fluid that is present in the first lumen 31 can leave the first fluid conduit 3 via the first end opening 32.

In the embodiment shown here, the port 100 also optionally includes a second fluid conduit 5 with at least one second lumen 51 and a second end opening 52. For the purpose of reference, the second end opening 52 in the embodiment of FIG. 1 is understood or referred to as a transition from an exterior Ä of the medical treatment apparatus 2000, only indicated in FIG. 1, to an interior of the port 100 or an interior I of the medical treatment apparatus 2000.

The first fluid conduit 3 is located, for example, in an interior of the second fluid conduit 5 and, with respect to the port 100, its first opening 32 is optionally located further inside the port 100 or the medical treatment apparatus 2000 only indicated in FIG. 1 (i.e., further inside) than the second opening 52 of the second fluid conduit 5.

The second end opening 52, which can be an opening plane, is provided in order to pass a section of a connector of a disposable, such as for example, the connector of a substitute fluid line 105 through it (see FIG. 2) into the interior of the port 100, with the aim of establishing a fluid communication between the first fluid conduit 3 and a connector lumen. The second end opening 52 is intended to guide the connector preferably in a positionally stable manner.

As intended the port 100 serves to establish a fluid communication between at least one fluid line 2002 of the treatment apparatus 2000, which is assigned to or faces or herein is included in the interior I of a medical treatment apparatus 2000, on the one hand, and the connector of a fluid line of a fluid-carrying disposable assigned to the exterior Ä of the treatment apparatus 2000, on the other hand. The connection is preferably made in an end section 1 of the port 100.

FIG. 1 shows a fastening section 2003 for attaching the port 100 to the medical treatment apparatus 2000, which is only indicated in FIG. 1. In FIG. 1, the port 100 passes through a housing section of a housing 2001 of the medical treatment apparatus 2000, which is limited by adjacent housing sections 2005.

DETAILED DESCRIPTION

FIG. 1 shows the port 100 in a state in which it is not connected to a connector. It is closed with a rinsing cap 200 as an example of a sealing device. FIG. 1 thus shows the port 100 in a "flush state" or "closed state" of the port 100.

The rinsing cap 200, which is placed on the port 100, closes the second end opening 52 and thus the interior of the port 100 as well as the two fluid conduits 3, 5 against an exterior Ä of the port 100 and/or the medical treatment apparatus 2000. For this purpose, an outer edge 202 of the rinsing cap 200 is placed fluid-tightly on or in the port 100. Thereby one front side 205 of the rinsing cap 200 faces the interior.

The rinsing cap 200 may have a groove 204 on or at its circumferential side, as explained in more detail below.

The housing 2001 optionally includes a rim 2007 completely or at least partially surrounding the fastening section 2003. The rim 2007 in turn includes a first section 2007*a* and a second section 2007*b*.

In an end region of the second lumen 51 opposite the second opening 52, at least one opening 54 may be provided on or in its side wall, which in FIG. 1 lies in front of the drawing plane and is therefore not shown due to the sectional view.

A leakage sensor is optionally provided to provide early notification in the event of a leakage, for example from the fluid communication established between the fluid line 2002 of the treatment apparatus 2000 on the one hand and the fluid line, such as the substitute fluid line 105, on the other hand. Appropriate voltage sources, lines, evaluation devices and alarm devices may be provided and suitably programmed where required.

The leakage sensor can be used to check whether the port 100 has been emptied of fluid as intended. Corresponding test routines, which evaluate signals from the leakage sensor, if present, and if necessary output actions or messages depending on the result of the check, can be programmed in the control device 150, for example.

FIG. 1 further shows a receiving section 2015 as part of an optional pivot lever of the medical treatment apparatus 2000. The receiving section 2015 of the pivot lever not otherwise shown in FIG. 1, which is indicated here by a screw, is used for detachably receiving at least a section of the optional rinsing cap 200 thereon.

Furthermore, an optional handle section 2013 of the pivot lever can be seen. It is used by the user to pull the rinsing cap 200 out of the port 100 by pulling on the handle section 2013 and in an axial direction (i.e., to the left in FIG. 1) and thereby to end the rinsing position.

It can be seen that the second lumen 51 of the second fluid conduit 5 in the optional embodiment shown includes at least one longitudinal section whose side walls (top and bottom in the sectional view of FIG. 1) are not parallel to one another in a direction along the centre line M or parallel thereto (left-right in FIG. 1) and/or do not have to be at a constant angle to one another. Rather, the cross-sectional area of the second lumen 51 always or even steadily increases over a certain distance, here exemplarily to the right, i.e., away from the second end opening 52.

The second lumen 51 optionally includes a first cross-sectional area limited by the side walls of the lumen 51, which is smaller than any other cross-sectional area of the second lumen 51 limited by the side walls of the lumen 51, which lies further towards the interior of the second lumen 51 than the first cross-sectional area, as can be seen at least from an area shortly before the first end opening 32, further to the right in FIG. 1. As a result, the second lumen 51 widens at least in sections towards the interior.

FIG. 1 further shows that the first lumen 31 can optionally end in a funnel-shape or diverging shape in the first end opening 32.

Figure 2:
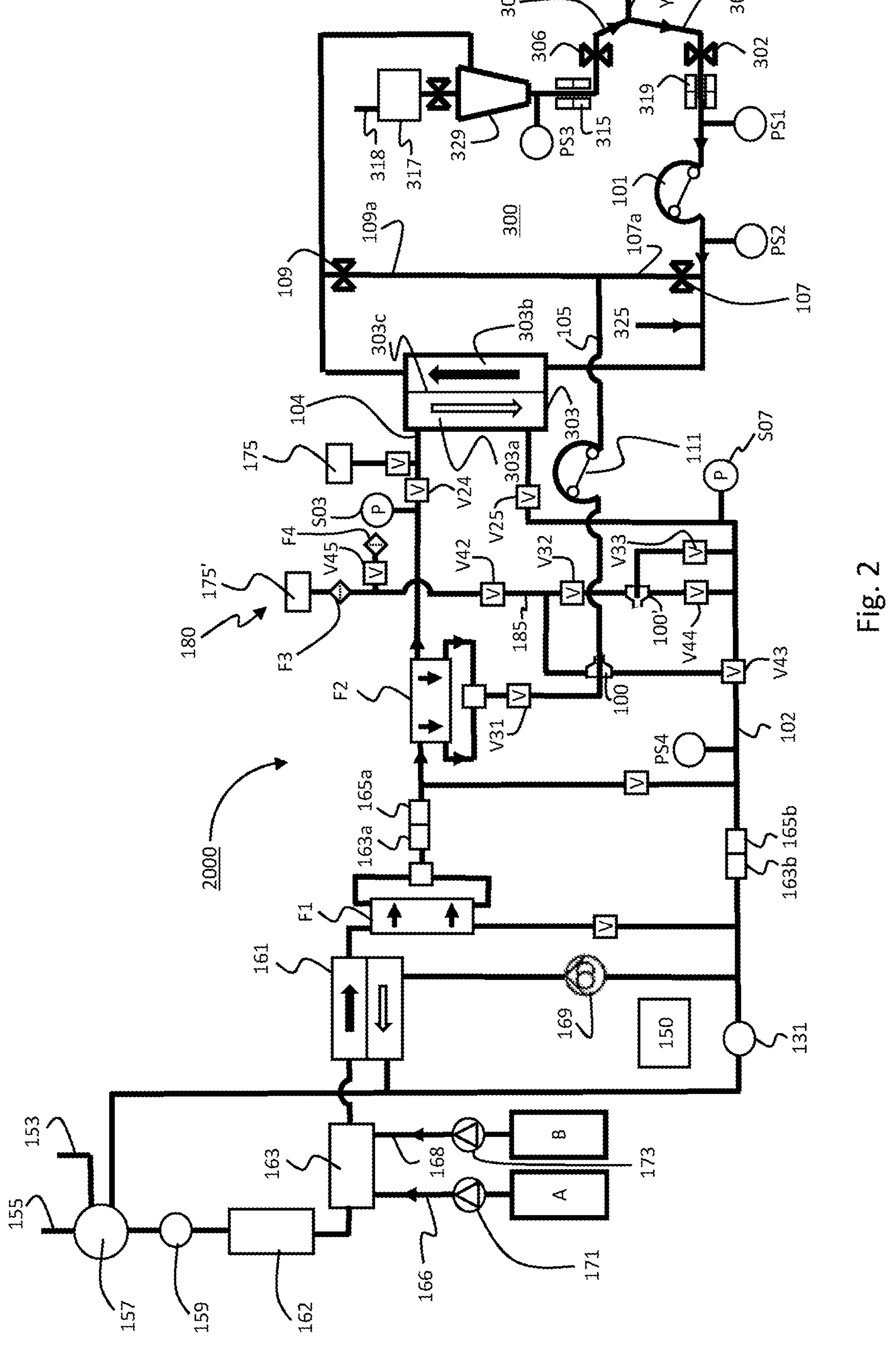
FIG. 2 shows a process flow chart of a medical treatment apparatus according to the present disclosure, for example that from FIG. 1.

A mouth of a sterile-air line 185 which is connected to a compressed-air source, for example, the second compressor 175', see FIG. 2, can be provided at an end of the second lumen 51 opposite to the second end opening 52, preferably on an upper side wall of the port 100.

After cleaning or disinfection and before opening the rinsing cap 200, sterile-air can be introduced via the sterile-air line 185 for connecting the disposable, and the cleaning or rinsing solution present in the port 100 can thus be largely removed. Compressed-air can also be introduced into the port 100 via the sterile-air line 185 for the reasons mentioned below and in particular as part of the methods or method steps mentioned herein.

From a cross-section in which also lies the opening plane of the first end opening 32 of the first lumen 31, the cross-sectional area of the second lumen 51 increases in the axial direction up to the beginning of an opening of the port which radially widens the second lumen 51 in at least one cross-section and/or in which the opening of the sterile-air line 185 lies, in the present example preferably always and/or steadily.

As can be seen from FIG. 1, the edge that limits the first opening 32 is optionally at a distance from the inner wall of the second lumen 51. This distance is at no point less than 5 mm, 6 mm, 7 mm or 8 mm. It can be seen that the distance is due to the widening of the second lumen 51 inward, that is to say to the right. If this widening of the second lumen 51 did not exist in this embodiment, the distance between the edge and the inner wall of the second lumen 51 would correspond to the difference between the radius of the outer circumferential surface of the first fluid conduit 3 and the radius of the inner circumferential surface of the second opening 52, in which the side surfaces limiting it are parallel and/or at a constant angle to each other. However, due to the widening, the distance here is greater. In the present example, it is at least 1.1 times this difference. The so achieved or enlarged step (compared to an embodiment without the widening shown in FIG. 1) serves to protect against a liquid bridge between liquid, which may have remained on the inner wall of the second lumen 51, and the first opening 31 of the first fluid conduit 3 and thus ultimately serves to protect the patient against germs transferred in this way.

FIG. 2 shows a process flow chart of an embodiment of the medical treatment apparatus 2000, in this case a blood treatment apparatus, connected to an extracorporeal blood circuit 300, which can be connected to the vascular system of the patient, not shown here, for treatment using double-needle access, or by using, for example, an additional Y-connector (reference numeral Y) using single-needle access. The blood circuit 300 may optionally be present in sections thereof in or on a blood cassette, which is referred to herein as an example of a disposable.

Pumps, actuators and/or valves in the area of the blood circuit 300 are connected to the treatment apparatus 2000 or for example to a control device 150 included by it.

The blood circuit 300 includes (or is connected to) an arterial patient tubing clamp 302 and an arterial connection needle of an arterial section or an arterial patient line, blood withdrawal line or of first line 301. The blood circuit 300 further includes (or is connected to) a venous patient tubing clamp 306 and a venous connection needle of a venous section, of a venous patient line, blood return line, or second line 305.

A blood pump 101 is provided in or on the first line 301, a substitute fluid pump 111 is connected to a dialysis liquid inlet line 104 for conveying fresh dialysis liquid, which is filtered in a further filter stage (F2) (substitute fluid). A substitute fluid line 105 can be fluidically connected to the inlet line 104. Via the substitute fluid pump 111, substitute fluid can be introduced by pre-dilution, via a pre-dilution valve 107, or by post-dilution, via a post-dilution valve 109, via associated lines 107*a* or 109*a* into line sections, for example into the arterial line section 301 or into the venous line section 305 (here between a blood chamber 303*b* of a blood filter 303 and a venous air separation chamber or venous blood chamber 329) of the blood circuit 300.

The blood filter 303 includes the blood chamber 303*b* connected to the arterial line section 301 and to the venous line section 305. A dialysis liquid chamber 303*a* of the blood filter 303 is connected to the dialysis liquid inlet line 104 leading to the dialysis liquid chamber 303*a* and to a dialysate outlet line 102, which guides dialysate, i.e., spent dialysis liquid, leading away from the dialysis liquid chamber 303*a*. Dialysis liquid chamber 303*a* and blood chamber 303*b* are separated from each other by a mostly semi-permeable membrane 303*c*. It represents the partition between the blood side with the extracorporeal blood circuit 300 and the machine side with the dialysis liquid or dialysate circuit, which is shown in FIG. 2 to the left of the membrane 303*c*.

The arrangement in FIG. 2 encompasses an optional detector 315 for detecting air and/or blood. The arrangement of FIG. 2 further encompasses one or two pressure sensors PS1 (upstream of the blood pump 101) and PS2 (downstream of the blood pump 101, it measures the pressure upstream of the blood filter 303 ("pre-hemofilter")) at the points shown in FIG. 2. Further pressure sensors may be provided, e.g., pressure sensor PS3 downstream of the venous bubble chamber 329.

An optional single-needle chamber 317 is used in FIG. 2 as a buffer and/or compensating reservoir in a single-needle procedure in which the patient is connected to the extracorporeal blood circuit 300 using only one of the two blood lines 301, 305.

The arrangement of FIG. 2 also encompasses an optional detector 319 for detecting air bubbles and/or blood.

An optional addition site 325 for Heparin may be provided.

On the left in FIG. 2 is shown a mixing device 163, which provides a predetermined mixture for the respective solution from the containers A (for A-concentrate via concentrate supply 166) and B (for B-concentrate via concentrate supply 168) for use by the treatment apparatus 2000. The solution contains water, heated e.g. by a heat exchanger 157, (on-line, e.g., as reverse osmosis water or from bags) from the water source 155.

A pump 171, which can be referred to as concentrate pump or sodium pump, is fluidically connected to the mixing device 163 and a source of sodium, for example the container A, and/or coveys out of it. An optional pump 173, which is assigned to the container B, for example for bicarbonate, can be seen.

The compressed-air source for building-up pressure in the port 100 can be embodied, for example, by the optional compressor with the reference numeral 175', which is also referred to herein non-restrictively as further compressor, and may be connected to the port 100 via the fluid line 185. Alternative sources of compressed-air may be provided for this purpose.

Furthermore, FIG. 2 shows a waste line 153 for the effluent. The optional heat exchanger 157 and a first flow pump 159, which is suitable for degassing, complete the arrangement shown.

A further pressure sensor may be provided as PS4 downstream of the blood filter 303 on the water side, but preferably upstream of the ultrafiltration pump 131 in the dialysate outlet line 102 for measuring the filtrate pressure or membrane pressure of the blood filter 303. Additional, optional pressure measuring points P may also be provided.

Blood leaving the blood filter 303 flows through an optional venous blood chamber 329, which may include a de-aeration device 318 and may be in fluid communication with the pressure sensor PS3.

The exemplary arrangement shown in FIG. 2 includes the control device or closed-loop control device 150. It may be in a wired or wireless signal connection with any of the components mentioned herein—especially or in particular with the blood pump 101—to control or regulate the treatment apparatus 2000.

By using the device for on-line mixing of the dialysis liquid, a variation of its sodium content, controlled by the control device or closed-loop control device 150, is possible within certain limits. For this purpose, in particular the measured values determined by conductivity sensors 163*a*, 163*b* may be taken into account. Should an adjustment of the sodium content of the dialysis liquid (sodium concentration) or of the substitute fluid turn out to be necessary or desired, this can be done by adjusting the conveying rate of the sodium pump 171.

In addition, the treatment apparatus 2000 includes devices for conveying fresh dialysis liquid and dialysate. A first valve may be provided between the first flow pump 159 and the blood filter 303, which opens or closes the inflow towards the blood filter 303 on the inlet side. A second, optional flow pump 169 is provided, e.g., downstream of the blood filter 303 which conveys dialysate to the drain line 153. A second valve may be provided between the blood filter 303 and the second flow pump 169, which opens or closes the outflow on the outlet side.

Furthermore, the treatment apparatus 2000 optionally includes a device 161 for balancing the flow flowing into and out of the dialyzer 303 on the machine side. The device 161 for balancing is preferably arranged in a line section between the first flow pump 159 and the second flow pump 169.

The treatment apparatus 2000 further includes devices, such as the ultrafiltration pump 131, for the precise removal of a volume of liquid from the balanced circuit, as predetermined by the user and/or by the control device or closed-loop control device 150.

Sensors such as the optional conductivity sensors 163*a*, 163*b* may be provided and serve to determine the conductivity, which in some embodiments is temperature-compensated, as well as the fluid flow upstream and downstream of the dialyzer 303.

Temperature sensors 165*a*, 165*b* may be provided as one or a plurality thereof. Temperature values supplied by them may be used to determine a temperature-compensated conductivity.

Further flow pumps in addition to or alternatively to, for example, the one with the reference numeral 169 may also be provided.

A number of optional valves are each denoted with V in FIG. 2.

In some embodiments, the control device 150 determines the electrolyte balance and/or liquid balance based on the measured values from the aforementioned optional sensors.

Filters F1 and F2 can be connected in series.

Even when using non-pure water, the filter F1 exemplarily serves herein to generate sufficiently pure dialysis liquid by the mixing device 163, which then flows through the blood filter 303, e.g. using the counter-current principle.

The filter F2 exemplarily serves here to generate sterile or sufficiently filtered substitute fluid from the sufficiently pure dialysis liquid leaving the first filter F1, by filtering, e.g., pyrogenic substances, in order to introduce it without hesitation into the patient's blood flowing extracorporeally and thus, finally, into the patient's body.

The treatment apparatus 2000 is optionally shown in FIG. 2 as a device for hemo(dia)filtration. However, hemodialysis apparatuses are also covered by the present disclosure, although possibly not specifically represented in a figure.

A possible position of the port 100 within the treatment apparatus 2000 according to the present disclosure can be seen.

The present invention is not limited to the embodiment described above; this serves for illustrative purposes only.

The arrows shown in FIG. 2 generally indicate the flow direction in FIG. 2.

As can be seen in FIG. 2, any number of ports can be provided. In the example of FIG. 2, these are two ports 100, 100'. What is described here for port 100 can also apply to the second port 100'.

The port 100 is, by way of example only, arranged at the end of the substitute fluid line 105.

The pressure sensor S07 is optionally used here for the pressure measurement in or to both ports 100, 100'. For this purpose, the valve V32 on the one hand and the valve V44 and/or the valve V33 on the other hand are opened.

In the example of FIG. 2, a compressed-air system 180 may be provided which includes a source of compressed-air, e.g., a compressor, for example the further compressor 175'. The further compressor 175' is in fluidic communication with one, or as here with both, of the ports 100, 100' via the sterile-air line 185. A filter F3 for sterile-air is preferably arranged in the sterile-air line 185. A further filter F4 for sterile-air can be provided at a connection of the sterile-air line 185 to the atmosphere.

In particular, the valves V24 in the line 104 upstream of the blood filter 303, the valve V25 in the line 102 downstream of the blood filter 303 and the V33, V44, V43, V42, V45 at the locations shown can be provided as valves.

What is stated herein, and in particular with respect to FIGS. 1 and 2, for port 100 may also apply to port 100' shown in FIG. 2.

The compressors 175 and 175' can be implemented using a common component or, as shown in FIG. 2, by separate compressed-air units.

Figure 3:
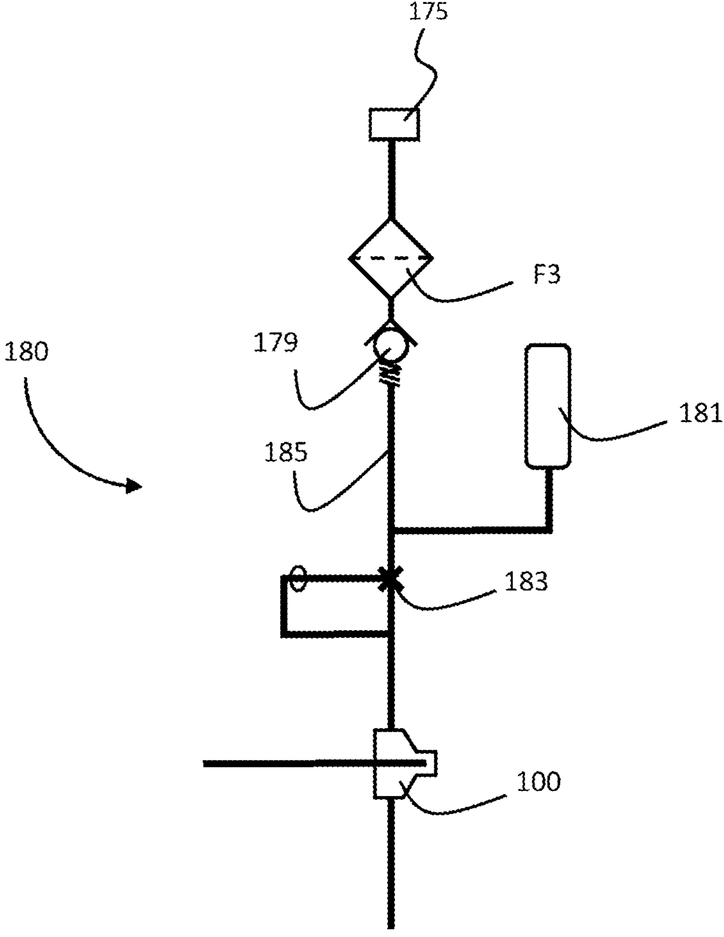
FIG. 3 shows, schematically simplified, the compressed-air system on the hydraulic side of FIG. 2.

FIG. 3 shows a simplified schematic of the compressed-air system 180 from FIG. 2 for the ports 100, 100'.

The compressed-air system 180 includes the compressor 175', preferably a filter F3, optionally the filter F4 shown in FIG. 2, which can form a connection to the atmosphere switchable via a valve, a non-return stop 179 (also: check valve), preferably further a compliance vessel 181 and in some embodiments a pressure reducer 183. The above components are arranged in or with fluid communication to the sterile-air line 185.

The backflow of compressed-air from the compliance vessel 181 in the direction of the compressor 175' is prevented by the non-return stop 179.

The pressure is fixed via the pressure reducer 183, preferably by a value between 20 hPa and 500 hPa, in such a way that as the port 100 is opened there is an uninterrupted flow of air out of the interior of the port 100 and into the atmosphere. The air flow quasi forms a "protective (gas) atmosphere" around the hygienically sensitive area of the first end opening 32.

Optionally, it may be provided that the compressor 175' only starts after the optional signal has been emitted or received and the compressor 175' has been prompted accordingly by the control device 150. In such embodiments, the compliance vessel 181 can serve to bridge the time until the compressor 175' builds up pressure by providing pressure from the compliance vessel 181.

Figure 4:
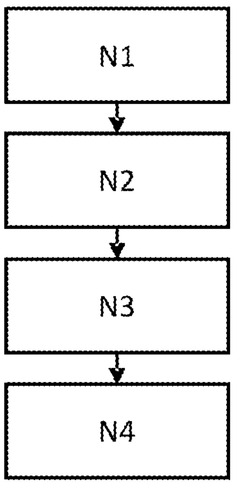
FIG. 4 shows, in a schematically simplified manner, a sequence of a method which can be initiated or executed via the control device and/or closed-loop control device of the medical treatment apparatus according to the present disclosure, in a first embodiment.

FIG. 4 shows a schematically simplified sequence of an exemplary embodiment of a method according to the present disclosure, which can be initiated or executed via the control and/or closed-loop control device 150 of the medical treatment apparatus 2000 according to the present disclosure, in a first embodiment.

Here, method step N1 represents a pumping out of liquid from the interior of the port 100, 100', preferably by the ultrafiltration pump 131 and/or with the sterile-air line 185 which is open to the atmosphere.

N2 represents closing the opening of the sterile-air line 185 to the atmosphere, for example by actuating one or more corresponding valves.

The method step N3 represents generating an overpressure in the second lumen 51 by the compressor 175', preferably at least the minimum overpressure.

N4 stands for the optional method step of checking whether the generated overpressure exceeds a predetermined threshold or maximum pressure. If this is the case, preferably after waiting for a stabilisation period, the method step N4 may possibly encompass an active lowering of the pressure, for example via the ultrafiltration pump 131.

Figure 5:
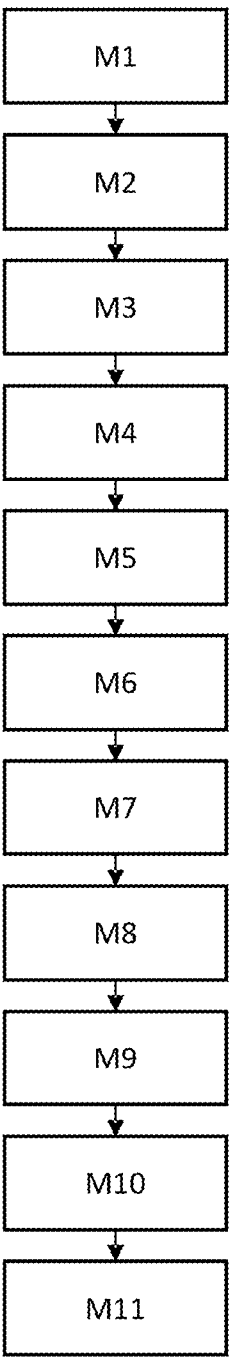
FIG. 5 shows a schematically simplified sequence of a method which can be initiated or executed via the control device and/or closed-loop control device of the medical treatment apparatus according to the present disclosure, in a second embodiment.

The checking of step N4 can be carried out, for example, by a pressure sensor such as the pressure sensor S07 shown in FIG. 2. This can be arranged downstream of the blood filter 303, upstream of the optional conductivity sensor 163*b* and/or upstream of the connection of the sterile-air line 185 with the dialysate outlet line 102, as shown in FIG. 2 as an example FIG. 5 shows a schematically simplified sequence of a method that can be initiated by the control and/or closed-loop control device 150 of the treatment apparatus 2000 according to the present disclosure in an exemplary embodiment.

Method step M1 thereby represents the removal of remaining (sterile) air from the balancing circuit of the treatment apparatus 2000. This removal can be carried out by rinsing the fluid lines of the balancing circuit. Here, the balancing circuit can be, include or be formed by the connection of the components balancing device 161, filter F1, filter F2, valve V24, valve V25, second flow pump 169. A bypass can be connected between valve V24 and valve V25 when the blood circuit is not connected, in particular before the port 100, 100' is opened (not shown in FIG. 2).

Method step M2 stands for venting the balancing circuit with sterile air in the direction of the drain.

The method steps M1 and M2 may also be referred to as preparation steps. They may be encompassed by the method in several embodiments, but not in other embodiments.

Method step M3 represents the venting, of both online ports 100, 100' and the dialysate outlet line 102 by switching on the compressor 175', while the valves V45, V42, V32 and V44 are opened, in particular by opening then to the atmosphere. Venting is continued until atmospheric pressure prevails inside the lines and the ports 100, 100'.

Method step M4 represents a closing of valve V45, which results in an increase in pressure within ports 100, 100' and the connected lines. When the pressure inside the lines and the ports reaches a predetermined threshold, for example 200 hPa, the compressor is stopped and the valve V42 is closed to prevent the pressure from increasing further, but also to prevent it from falling.

In method step M5, the pressure in the port is measured, preferably after a predetermined stabilisation time, i.e., a time that takes into account fluctuations and initial measurement inaccuracies due to pressure changes. If this pressure, also referred to herein as the final pressure, exceeds an upper threshold or an upper maximum pressure, for example 300 hPa, the pressure is reduced, for example by individual strokes of the ultrafiltration pump 131, until it is again below this maximum pressure.

The method step M6 represents a waiting time of, e.g., five seconds.

In method step M7, a first average pressure P1 is determined over one second.

The method step M8 represents a waiting time of, e.g., 24 seconds.

In method step M9, a second average pressure P2 is determined over one second.

Method step M10 represents the calculation of a repetition time T according to the following formula:

$$T = 25s * \frac{50\ \text{hPa}}{(P1 - P2)}$$

where 50 hPa is the permissible pressure drop, selected as an example, until the next pressure increase in the port.

Method step M11 represents evaluating the result of the calculation from method step M10 with subsequent output of the evaluation, for example, namely Error, if T<60 s, as then the leakage is too large;

T, if 60 s≤T≤1800 s; and

T=1800 s, if T>1800 s and causing the compressor 175' to repeatedly build-up pressure based on the times resulting from the evaluation, provided there is no error.

LIST OF REFERENCE NUMERALS

100 port

100' port

3 first fluid conduit (inside)
5 second fluid conduit (outside)
31 first lumen
32 first end opening
51 second lumen
52 second end opening
54 opening, e.g. groove
Ä exterior
I interior
M mid line or centre line
2000 medical treatment apparatus
2001 housing
2002 fluid line
2003 fastening section
2005 adjacent housing sections
2007 edge
2007 *a* first section
2007 *b* second section
2013 handle section
2015 receiving section
101 blood pump
102 dialysate outlet line
104 dialysis liquid inlet line
105 substitute fluid line
107 pre-dilution valve
107 *a* line belonging to pre-dilution valve
109 post-dilution valve
109 *a* line belonging to post dilution pump
111 substitute fluid pump
131 ultrafiltration pump
150 control device
153 drain or waste line
155 water source
157 heat exchanger
159 first flow pump
161 balancing device
163 *a* conductivity sensor
163 *b* conductivity sensor
165 *a* temperature sensor
165 *b* temperature sensor
166 concentrate supply
168 concentrate supply
169 second flow pump
171 pump, sodium pump
173 pump, bicarbonate pump
175 compressor
175' compressor
179 non-return stop
180 compressed-air system
181 compliance vessel
183 pressure reducer
185 sterile-air line
200 rinsing cap
202 outer edge of rinsing cap
204 first groove
205 front side of rinsing cap
300 extracorporeal blood circuit
301 first line (arterial line section)
302 first tubing clamp
303 blood filter or dialyzer
303 *a* dialysis liquid chamber
303 *b* blood chamber
303 *c* semi-permeable membrane
305 second line (venous line section)
306 second tubing clamp
315 detector
317 single-needle chamber
318 de-aeration device
319 detector
325 addition site for Heparin
329 venous blood chamber (optional); venous bubble chamber (optional)
F1 filter
F2 filter
F3 sterile-air filter
F4 sterile-air filter
A container
B container
D predetermined time period
P pressure measurement sites
PS1 arterial pressure sensor (optional)
PS2 arterial pressure sensor (optional)
PS3 pressure sensor (optional)
PS4 pressure sensor for measuring the filtrate pressure (optional)
N1 to N4 method steps
M1 to M11 method steps
V valves
V24 valve
V25 valve
V31 valve
V32 valve
V33 valve
V42 valve
V43 valve
V44 valve
V45 valve
Y Y-connector

The invention claimed is:

1. A medical treatment apparatus comprising:

at least one port for establishing fluid communication between at least one fluid line of the medical treatment apparatus assigned to an interior of the medical treatment apparatus and a connector of a fluid line of a disposable assigned to an exterior of the medical treatment apparatus, wherein the at least one port comprises:

a first lumen fluidly connected to a fluid line of the at least one fluid line, the first lumen having a first end opening; and a second lumen having a second end opening, wherein the first lumen is located further inside the at least one port than the second lumen in a radial and axial direction;

a sealing device for sealing an interior of the port from the exterior of the treatment apparatus;

a compressed-air source for introducing air or sterile-air into the port along at least one sterile-air line; and a control device programmed to cause the compressed-air source to build-up and maintain a predetermined minimum overpressure in the sterile-air line, in the compressed-air source and/or inside the port.

2. The medical treatment apparatus according to claim 1, wherein the sealing device comprises a rinsing cap.

3. The medical treatment apparatus according to claim 1, wherein the control device is programmed, upon reaching a predetermined program section of a program run by the control device for controlling or regulating the treatment apparatus, to cause the compressed-air source to build-up and/or maintain the predetermined minimum overpressure in the sterile-air line, in the compressed-air source, and/or inside the port.

4. The medical treatment apparatus according to claim 1, wherein the compressed-air source comprises or is a compressor and/or a compliance vessel.

5. The medical treatment apparatus according to claim 1, wherein the control device is programmed to not further increase the pressure in the sterile-air line, the compressed-air source, and/or the port once the predetermined minimum overpressure is reached.

6. The medical treatment apparatus according to claim 1, further comprising a detection device for detecting that an action to close and/or to open the port to the exterior of the treatment apparatus has just taken place, and for emitting a corresponding signal to the control device which is programmed, upon receiving the signal, to cause the compressed-air source to build-up and/or maintain the predetermined minimum overpressure.

7. The medical treatment apparatus according to claim 6, wherein the detection device comprises:

a pressure sensor arranged for determining the pressure prevailing in the sterile-air line, the compressed-air source, and/or the port and for collecting a pressure value when determining the pressure; and/or a switch; and wherein the detection device evaluates a pressure profile or a pressure change that results from pressure values measured via the pressure sensor at different times, and/or registers the actuation of the switch, in order to emit a signal based on the evaluation of the pressure profile or the pressure change and/or based on the actuation of the switch.

8. The medical treatment apparatus according to claim 1, wherein the control device is programmed to generate an overpressure in the sterile-air line, the compressed-air source, and/or in the port, after the overpressure has been generated, to determine a pressure drop or a pressure drop rate, and based on the determined pressure drop or pressure drop rate, to determine when pressure is to be built up again using the compressed-air source in order to achieve or maintain at least the minimum overpressure.

9. The medical treatment apparatus according to claim 8, wherein the overpressure comprises the predetermined minimum overpressure.

10. The medical treatment apparatus according to claim 1, further comprising a negative pressure source which is in fluid communication with the port, wherein the control device and/or closed-loop control device is programmed to generate negative pressure in the port or to lower a pressure prevailing in the port.

11. The medical treatment apparatus according to claim 10, wherein the control device is programmed to generate the negative pressure in the port or to lower the pressure prevailing in the port down to the minimum overpressure.

12. The medical treatment apparatus according to claim 11, wherein the control device is programmed to generate the negative pressure in the port or to lower the pressure prevailing in the port such that the pressure in the port is not lower than the minimum overpressure.

13. The medical treatment apparatus according to claim 11, wherein the control device is programmed to generate the negative pressure in the port or to lower the pressure prevailing in the port if the pressure in the sterile-air line, the compressed-air source, and/or in the port exceeds a predetermined threshold or maximum pressure.

14. A method for preparing the operation of or for operating a medical treatment apparatus according to claim 1, the method comprising:

generating a closed volume or space comprising the interior of the port or a partial volume thereof, including lines which are in fluid communication with the interior of the port, by actuating components of the treatment apparatus, or by generating an overpressure in the closed volume via the compressed-air source.

15. The method according to claim 14, further comprising pumping off liquid from the interior of the port.

16. The method according to claim 15, wherein pumping off the liquid comprises using an ultrafiltration pump and/or pumping with the sterile-air line open to the atmosphere.

17. The method according to claim 14, wherein the overpressure comprises at least the pre-determined minimum overpressure.

18. The method according to claim 14, further comprising:

measuring the pressure prevailing in the port and/or in the sterile-air line after a pre-determined time has been allowed to elapse; and determining a pressure loss or rate of pressure loss based on generated overpressure and measured pressure.

19. The method according to claim 18, further comprising:

calculating a repetition time after which, once the repetition time has elapsed, the pressure in the port and/or in the sterile-air line is increased again at least up to the minimum overpressure via the compressed-air source.

20. The method according to claim 19, further comprising repeatedly building-up pressure via the compressed-air source at intervals based on the calculated repetition time.

21. A control device which is programmed to initiate the execution of a method according to claim 14 in interaction with a medical treatment apparatus.

22. A medical blood treatment apparatus having a control device according to claim 21.

23. A computer program product with a program code stored on a machine-readable carrier, configured to configure a control device of a conventional medical treatment apparatus in such a way that the medical treatment apparatus becomes a medical treatment apparatus with a control device and/or closed-loop control device according to claim 21.

* * * * *